(12) United States Patent
Bucevschi et al.

(10) Patent No.: US 7,985,819 B2
(45) Date of Patent: Jul. 26, 2011

(54) STYRENE-MALEIC ANHYDRIDE COPOLYMERS FOR BIOAPPLICATIONS AND THEIR PREPARATION

(75) Inventors: Mircea Dan Bucevschi, Rehovot (IL); Monica Colt, Rehovot (IL)

(73) Assignee: Exotech Bio Solutions Ltd., Kiryat Gat (IL)

( * ) Notice: Subject to any disclaimer, the term of this patent is extended or adjusted under 35 U.S.C. 154(b) by 0 days.

(21) Appl. No.: 12/411,522

(22) Filed: Mar. 26, 2009

(65) Prior Publication Data

US 2009/0318649 A1    Dec. 24, 2009

Related U.S. Application Data

(63) Continuation of application No. 12/295,512, filed as application No. PCT/US2007/065633 on Mar. 30, 2007, now abandoned.

(60) Provisional application No. 60/787,191, filed on Mar. 30, 2006.

(51) Int. Cl.
   *C08F 4/32*    (2006.01)
   *C08F 222/08*  (2006.01)

(52) U.S. Cl. ..... 526/213; 526/272; 526/227; 526/232.1; 526/229; 526/219.6; 526/218.1; 526/223

(58) Field of Classification Search .......... 526/213, 526/272, 227, 232.1, 229, 219.6, 218.1, 223
See application file for complete search history.

(56) References Cited

U.S. PATENT DOCUMENTS

| | | |
|---|---|---|
| 2,047,398 A | 7/1936 | Voss et al. |
| 2,205,882 A | 6/1940 | Graves |
| 2,286,062 A | 6/1942 | Condo et al. |
| 2,378,629 A | 6/1945 | Hanford |
| 2,866,775 A | 12/1958 | Sellers et al. |
| 2,897,121 A | 7/1959 | Wagner et al. |
| 2,971,939 A | 2/1961 | Baer et al. |
| 3,157,595 A | 11/1964 | Johnson et al. |
| 3,939,108 A | 2/1976 | Sirota et al. |
| 3,980,663 A | 9/1976 | Gross |
| 3,989,586 A | 11/1976 | Bashaw et al. |
| 4,051,311 A | 9/1977 | Lee |
| 4,105,649 A | 8/1978 | Evani et al. |
| 4,126,549 A | 11/1978 | Jones et al. |
| 4,145,375 A | 3/1979 | Cutter et al. |
| 4,153,682 A | 5/1979 | Ackers |
| 4,381,784 A | 5/1983 | Aberson et al. |
| 4,390,672 A | 6/1983 | von Bonin |
| 5,221,787 A | 6/1993 | Robison et al. |
| 6,127,451 A | 10/2000 | Qian |
| 6,590,019 B2 | 7/2003 | Dheret et al. |
| 2007/0142585 A1 * | 6/2007 | Moore .......... 526/266 |

FOREIGN PATENT DOCUMENTS

| | | |
|---|---|---|
| EP | 0052274 A2 | 5/1982 |
| EP | 0433711 A2 | 6/1991 |

OTHER PUBLICATIONS

Sethi, N., et al., "Safety Evaluation of a Male Injectable Antifertility Agent, Styrene Maleic Anhydride, In Rats," Contraception, 39(2):217-226, 1989.
Lohiya, N.K., et al., "Repeated vas occlusion and non-invansive reversal with styrene maleic anhydride for male contraception in langur monkeys," Int. J. Androl, 23:36-42, 2000.
Rong, Y., et al., "Microcapsules with compact membrane structure from gelatin and styrene-maleic anhydride copolymer by complex coacervation," Colloids and Surfaces A:Physiochem. Eng. Aspects, 242:17-20, 2004.
Patel, H, et al., "Polymeric prodrug: Synthesis, release study and antimicrobial property of poly(styrene-co-maleic anhydride)-bound acriflavine," Die Angewardte Makromoleculare Chemie, 263:25-30, 1998.
Patel, J.S., et al., "Bioactive polymers: Synthesis, release study and antimicrobial properties of polymer bound Ampicillin," Die Angewandt, Mak. Chem, 271:24-27, 1999.
Ottenbrite, R.M., "Antitumor Activity of Polycarboxylic Acid Polymers," J. Macromol. Sci-Chem., A22(5-7):819-832, 1985.
Spridon, D., "Synthesis and Biocompatibility of Maleic Anhydride Copolyers:1. Maleic Anhydride-Vinyl Acetate, Maleic Anhydride-Methyl Methacrylate and Maleic Anhydride-Styrene," Polymer Int. 43:175-181, 1997.

* cited by examiner

*Primary Examiner* — Robert D. Harlan
(74) *Attorney, Agent, or Firm* — Elmore Patent Law Group, P.C.; Edgar W. Harlan; Carolyn S. Elmore

(57) ABSTRACT

The present invention discloses styrene-maleic anhydride copolymers preparations using solventless techniques. The solventless method resulted in reduced amounts of residues, such as unreacted styrene and/or maleic anhydride monomers, which makes the copolymers particularly suitable for bioapplications.

24 Claims, No Drawings

STYRENE-MALEIC ANHYDRIDE COPOLYMERS FOR BIOAPPLICATIONS AND THEIR PREPARATION

RELATED APPLICATIONS

This application is a continuation of U.S. application Ser. No. 12/295,512 filed Mar. 30, 2007, which is a US National stage entry of International Application No. PCT US07/065, 633, which designated the United States and was filed on Mar. 30, 2007, published in English, which claims the benefit of U.S. Provisional Application No. 60/787,191 filed Mar. 30, 2006.

FIELD OF THE INVENTION

The invention relates to, in part, styrene-maleic anhydride copolymers. It relates to methods of synthesizing such polymers using bulk polymerization methods which yield partially hydrolysed polymers in acidic form. The invention also relates to methods of preparing styrene-maleic anhydride copolymers that have a low residual content of monomers (styrene and maleic acid) and which are suited to bioapplications as solutions, hydrogels or solids for medical bioengineering, tissue engineering, pharmaceutical products, hygienic care, cosmetics, biotechnology, food industry, agriculture, absorbent textiles and the like.

BACKGROUND OF THE INVENTION

Styrene-maleic anhydride copolymers (SMA copolymers) are used in numerous applications but their use in bio-applications is hindered by their lack of purity and residual hazardous contaminates.

The FDA approved SMA copolymers as indirect food additives for use as articles or components of articles that contact food items (Code of Federal Regulations, Sec. 177.1820 "Styrene-maleic anhydride copolymers", Title 21, Volume 3 p 304-305, revised as of Apr. 1, 2000). The FDA specified that SMA copolymers have a minimum average molecular mass of 70,000 and contain not more that 15 weight percent maleic anhydride, 0.3 weight percent residual styrene monomer, 0.1 weight percent residual maleic anhydride monomer, 0.006 weight percent maximum extractible fractions in distillated water at reflux temperature for 1 hr, and 0.02 weight percent maximum extractible fractions in n-heptane at 73° F. for 2 hr.

Sethi, N. et al. demonstrated the biocompatibility of SMA commercial products, but a multistep, complex purification procedure was required before utilization. Sethi, N. et al. *Contraception* 1989, 39, 217-226. The same conclusion was reported by Lohiya, N. K et al. Lohiya, N. K. et al. *Int. J. Androl.* 2000, 23, 36-42.

Wagner J. G. et al in U.S. Pat. No. 2,897,121 and Chen, Y. R. et al in *Colloids and Surfaces A: Physicochem. Eng. Aspects*, 2004, 242, 17-20 present the utilization of SMA copolymers as additives for a pharmaceutical carrier for oral administration. Although the authors assert that the polymers can be used for bio-applications, supporting data, such as purity, is not presented.

Patel, H. A. et al. disclose the synthesis, release study, and antimicrobial properties of acriflavine bound to SMA. Patel, H. A. et al. *Die Angewandte Makromolekulare Chemie* 1998, 263, 25-30. Patel, H. A. et al. report similar findings for SMA bound ampicillin. Patel, H. A. et al. *Die Angewandte Makromolekulare Chemie* 1999, 271, 24-27. In both cases, advanced purification of the SMA copolymer was necessary to make the composition suitable for bio-application.

Ottenbrite, R. M. and Spiridon, D. disclose the use of SMA copolymers as antitumor effectors. Ottenbrite, R. M. and Spiridon, D demonstrate the biocompatibility of the SMA copolymers but only after rigorous purification steps. Ottenbrite, R. M. *J. Macromol. Sci.-Chem.* 1985, A22 (5-7), 819-832; Spiridon D. *Polymer International,* 1997, 43, 175-181.

U.S. Pat. No. 3,980,663 and U.S. Pat. No. 4,381,784 disclose using SMA copolymers as water absorbing materials for hygienic care. U.S. Pat. No. 3,939,108 and U.S. Pat. No. 6,590,019 disclose SMA copolymers as an adhesive useful for bottle labeling. U.S. Pat. No. 5,080,888 discloses SMA copolymers in cosmetics. U.S. Pat. No. 4,980,403; U.S. Pat. No. 5,104,957; U.S. Pat. No. 5,480,427; and U.S. Pat. No. 6,127,451 disclose using SMA copolymers as biomaterials. U.S. Pat. No. 4,153,682; U.S. Pat. No. 6,500,447; and U.S. Pat. No. 6,531,160 disclose using SMA copolymers in pharmaceutical products as drug delivery systems.

A condition for using SMA copolymers in a bio-application is that its chemical purity be as high as possible, while its hazardous contaminant content be as low as possible. Contamination of SMA copolymers has two causes derived from the polymerization processes used: 1) non-reacted monomers, and 2) auxiliaries of polymerization such as: organic solvents, initiators . . . etc.

For example, SMA copolymers are prepared mainly by solvent based methods, but these methods are also the most contaminating because, besides unreacted monomers and initiators, there is residual solvent to remove. See U.S. Pat. No. 2,286,062; U.S. Pat. No. 2,378,629; U.S. Pat. No. 2,866,775; U.S. Pat. No. 3,157,595; U.S. Pat. Nos. 3,989,586; 4,105,649; and U.S. Pat. No. 4,126,549. The additional purification steps required represent an important economical restriction to using SMA copolymers in bio-applications compared to other category of polymers.

Bulk polymerization is less contaminating than solution polymerization because there are no organic solvents. See Voss, A. et al. in U.S. Pat. No. 2,047,398; Graves, G. D. in U.S. Pat. No. 2,205,882 and Lee Y. C. et al. in U.S. Pat. No. 4,051,311 disclosing maleic anhydride copolymers of styrene, vinyl acetate, and others by bulk polymerization methods, with and without peroxidic initiators. The content of maleic anhydride monomers is less than 55% by weight in the initial mixture of comonomers. Baer, M. in U.S. Pat. No. 2,971,939 presents the synthesis of styrene maleic anhydride copolymers with a content of maleic anhydride less than 12% by weight using bulk polymerization methods. In these disclosures, a mixture of styrene and peroxidic initiator is allowed to homopolymerize until a 3-5% conversion. At this point, maleic anhydride monomer is added at a constant rate to form a maleic anhydride in styrene solution. The SMA copolymer is then extracted from the reaction mass with benzene and ultimately separated from the solution by precipitation with methanol.

Disadvantages with these bulk polymerization methods include a) incomplete conversion of monomers to copolymer due to increasing impedance of diffusion of the reactants to reaction centers because of increasing reaction mass viscosity; b) purification to remove non-reacted monomer is difficult and realized by dissolution into specific solvents (such as acetone or benzene), followed by precipitation, extraction with alcohols or water, and drying; c) generation of large amounts of reaction heat risking explosion; d) handling of reaction mass is difficult; and e) purification solids after precipitation by extraction is neither cost effective nor ecologically friendly.

Cutter, L. A. in U.S. Pat. No. 4,145,375 presents a process for copolymerizing styrene and maleic anhydride which involves a sequence of operations in which maleic anhydride is first gradually admixed with styrene in a mass stage under polymerizing conditions to rapidly form styrene-maleic anhydride polymer. The styrene-rich mixture is then suspended in water and the styrene polymerization completed as in a conventional mass/suspension polymerization system. The suspension step further modifies the polymer by opening the anhydride group to form free carboxylic acid groups on the polymer chain. Following the heating period, the polymerization mixture is cooled; the polymer beads are separated from the water by a solid-bowl centrifuge, and dried in a rotary air drier. The polymers resulted have Mw=100,000-500,000, and the content of residual styrene is between 0.02 and 0.1% by weight. A disadvantage of this process is that the final product is a blend of polystyrene and SMA copolymer, the polystyrene being a major contaminant, with multiple implications making it unfavorable for bio-applications. Similar problems exist for front polymerization which uses excess of styrene. Szalay, J. et al., *Macromol. Rapid Commun.* 1999, 20, 315-318.

Methods of copolymerization of maleic anhydride and other monomers in an aqueous medium have been disclosed. See Bomer B. et al. in U.S. Pat. No. 4,737,549; Saraydin D. et al. in *J. Appl. Polym. Sci.* 2001, 79, 1809-1815; Caycara, T. et al. in *J. Polym. Sci. A: Polym. Chem.* 2001, 39, 277-283; Akkas, P. et al. in *J. Appl. Polym. Sci.* 2000, 78, 284-289; Sen, M. et al. in *Polymer* 1999, 40, 913-917; Sen, M. et al. in *Polymer* 1998, 39, 1165-1172; Karadag, E. et al. in *J. Appl. Polym. Sci.* 1997, 66, 733-739; Saraydin, D. et al. in *Biomaterials* 1994, 15, 917-920; and Karadag, E. et al. in *Biomaterials* 1996, 17, 6770. However, these methods cannot be used for copolymerizing styrene due to the differences in solubility of the two comonomers. Additionally, the resulting polymer will have few carboxylic groups, limiting the number of potential bio-applications.

Copolymerization yields are highest (approximately 95%) when using equimolecular monomer feeds, and with processes that achieve good mass transfer of reactants (such as those achieved by polymerization in organic solvent media). Processes that don't use equimolecular monomer feeds induce a high value of conversion only for the monomer which is present in the least amount. Klumperman, B. et al. *Polymer* 1993, 34, 1032-1037; Klumperman, B. *Macromolecules*, 1994, 27, 6100-6101; Klumperman, B. et al. *Eur. Polym. J.* 1994, 30, 955-960.

The most difficult aspect of purifying SMA copolymers is removal of unreacted styrene because it is an organic compound liquid, insoluble in water, but soluble in organic solvents with high boiling points that make it difficult to dry, even in high vacuum. Boundy, R. H. "Styrene, its polymers, Copolymers and Derivatives," Reinhold Publishing Corporation, New York, 1952, pp. 860-865.

Unreacted maleic anhydride can be removed by simple hydrolysis with water to form maleic acid which has a high solubility in water (greater than $4.4 \times 10^5$ ppm(wt) at 25° C.; Yaws C. L. in "Chemical Properties Handbook" McGraw-Hill Companies, Inc. New York, 1999), allowing its efficient and economical elimination from copolymers. In addition, the rate of hydrolysis of free maleic anhydride is much higher than that of polymerized maleic anhydride. Ratzch, M. et al. *J. Macromol. Sci-Chem.* 1987, A24, 949-965; Wang, M. et al. *J. AppL. Polym. Sci.* 2000, 75, 267-274.

SUMMARY OF THE INVENTION

In one aspect, the invention relates to a styrene-maleic anhydride copolymer having less than 0.050% by weight unreacted styrene monomer.

In a further embodiment, the styrene-maleic anhydride copolymer has less than 0.090% by weight unreacted maleic anhydride and maleic acid combined.

In a further embodiment, the weight percent of styrene monomer to maleic anhydride and maleic acid monomer as defined as styrene/(maleic anhydride+maleic acid) is 42:58-52:48.

In a further embodiment, the viscosimetric molecular weight, $M_v$, of the styrene-maleic anhydride copolymer is 200,000-2,500,000.

In a further embodiment, the amount of unreacted styrene in the styrene-maleic anhydride copolymer is 0.015% to 0.042% by weight.

In a further embodiment, the amount of unreacted maleic anhydride and maleic acid combined in the styrene-maleic anhydride copolymer is 0.045% to 0.2% by weight.

In another aspect, the present invention relates to a medicament comprising the styrene-maleic anhydride copolymers of the present invention.

In another aspect, the present invention relates to an article of manufacture comprising the styrene-maleic anhydride copolymers of the present invention.

In a further embodiment, the article of manufacture is used in the field of medical bioengineering, tissue engineering, pharmaceutical products, body hygiene, cosmetics, biotechnology, food industry, agriculture, or absorbent textiles.

In another aspect, the present invention relates to a method of preparing a styrene-maleic acid copolymer comprising: a) melting an amount of maleic anhydride monomer; b) adding an amount of styrene containing dissolved initiator to the maleic anhydride; and c) stirring the maleic anhydride, styrene, and initiator mixture for an effective amount of time to form a styrene-maleic acid copolymer.

In a further embodiment, the initiator is a free radical initiator.

In a further embodiment, the initiator is selected from the group consisting of diacyl peroxides, dibenzoyl peroxide, di-tertbutyl peroxide, tert-butyl perbenzoate, tert-butyl perethylhexanoate, peresters, tert.-butyl perpivalate, aliphatic azo, azoisobutyronitrile, azo-4-cyanopentanoic acid, peroxodisulphuric acid, and hydrogen peroxide.

In a further embodiment, the initiator is dibenzoyl peroxide or azoisobutyronitrile.

In a further embodiment, during synthesis the amount of styrene: maleic anhydride is between 1:6 and 1:14 by weight.

In a further embodiment, during synthesis the amount of styrene: maleic anhydride is between 1:8 to 1:12 by weight.

In a further embodiment, the amount of initiator is between 0.01% and 0.05% versus the weight of the reaction mass.

In a further embodiment, the amount of initiator is between 0.025% and 0.035% versus the weight of the reaction mass.

In a further embodiment, melting the maleic anhydride is carried out by heating the maleic anhydride at least to 75° C.

In a further embodiment, the styrene is added to the maleic anhydride between 55° C. and 100° C.

In a further embodiment, the styrene is added to the maleic anhydride between 65° C. and 90° C.

In a further embodiment, the styrene is added to the maleic anhydride over a period of time between 10 minutes and 60 minutes.

In a further embodiment, the styrene is added to the maleic anhydride over a period of time between 20 and 40 minutes.

In a further embodiment, the mixing of the maleic anhydride, styrene, and initiator is carried out at atmospheric pressure and at a temperature between 60° C. and 150° C. for a period of time between 45 minutes and 300 minutes.

In a further embodiment, the mixing of the maleic anhydride, styrene, and initiator is carried out at atmospheric pressure and at a temperature between 85° C. and 115° C. for a period of time between 60 and 180 minutes.

In a further embodiment, the method further comprises the step of allowing the styrene-maleic anhydride copolymer formed in step c) to cool to a temperature between 55° C. and 85° C.

In a further embodiment, the styrene-maleic anhydride copolymer formed in step c) is cooled to between 60° C. and 80° C.

In a further embodiment, the method further comprise hydrolyzing at least a portion of the maleic anhydride to maleic acid by adding water to the styrene-maleic anhydride copolymer.

In a further embodiment, the amount of water is between 5% and 40% by weight of the styrene-maleic anhydride copolymer.

In a further embodiment, the amount of water is between 10% and 35% by weight of the styrene-maleic anhydride copolymer.

In a further embodiment, the water is added over a period of time between 30 and 180 minutes.

In a further embodiment, the water is added over a period of time between 60 and 120 minutes.

In a further embodiment, after the water is added to the copolymer the mixture is mixed for a period of time between 20 and 90 minutes.

In a further embodiment, the mixture is mixed for a period of time between 30 and 60 minutes.

In a further embodiment, the method further comprises allowing the copolymer to cool to room temperature.

In a further embodiment, the method further comprises purifying the copolymer by extracting free maleic acid with water.

In a further embodiment, the copolymer is mixed with a quantity of water about 6 times the weight of the copolymer at a temperature between 5° C. and 40° C. before removing the water.

In a further embodiment, the copolymer is mixed with the water at a temperature between 15° C. and 35° C.

In a further embodiment, the copolymer is mixed with the water for a period of time between 1 and 6 hours before removing the water.

In a further embodiment, the copolymer is mixed with the water for a period of time between 2 and 4 hours before removing the water.

In a further embodiment, the water is removed by filtration under pressure.

In a further embodiment, the extraction is repeated until the content of maleic acid in the supernatant is less than 0.001% by weight.

In a further embodiment, the method further comprises a drying step wherein the copolymer is dried at a temperature between 50° C. and 90° C.

In a further embodiment, the copolymer is dried at a temperature between 60° C. and 80° C.

In a further embodiment, the copolymer is dried under vacuum of 50 mbar or less.

In a further embodiment, the copolymer is dried for a period of time between 4 and 10 hours.

In a further embodiment, the copolymer is dried for a period of time between 6 and 8 hours.

DETAILED DESCRIPTION OF THE INVENTION

Definitions

The term "bio-applications" as used herein refers to all applications for which the most important property is biocompatibility.

The term "biocompatibility" as used herein refers to biochemical characteristics which a material possess that make it acceptable to living organisms (human, animals and plants), as an integral part of them, without have spontaneous or in time the manifestation of some repulsive or toxic phenomena under the form of inflammation, infections and others (Black J., "Biological Performance of Materials: Fundamentals of Biocompatibility", 2 d ed. M. Dekker, N.Y., 1992). This interpretation is given both to pure materials (100% purity, other substances not detected) and those that have a purity less than 100% (because they contain contaminants).

The standards that have guided biocompatibility testing are the 1) Tripartite Guidance; 2) the International Organization for Standardization (ISO) 10993 standards (which are known as the Biological Evaluation of Medical Devices and remain under development internationally); and 3) the FDA Blue Book Memoranda.

Methods of Polymerization

In one embodiment, the present invention relates to a process of obtaining styrene-maleic-anhydride copolymers using bulk-polymerization methods and free-radical initiators, with monomer feeds of styrene (Sty):maleic anhydride (MAnh) of 1:6, 1:14, 1:8, or 1:12 and a quantity of initiator not less than 0.01% and not more than 0.05% versus the reaction mass. In another embodiment, the quantity of initiator is not less than 0.025% and not more than 0.035%.

Examples of suitable initiators for initiating polymerization are the customary agents which form free radicals by thermal decomposition. Non-limiting examples include: diacyl peroxides, such as dibenzoyl peroxide, di-tertbutyl peroxide, tert-butyl perbenzoate or tert-butyl perethylhexanoate peresters, such as tert-butyl perpivalate, aliphatic azo compounds, such as azoisobutyronitrile, azo-4-cyanopentanoic acid or other water-soluble aliphatic azo compounds, salts of peroxodisulphuric acid or hydrogen peroxide. In one embodiment, the initiator is dibenzoyl peroxide and azoisobutyronitrile.

Polymeric reactions are carried out in a kneader-extruder connected to a vacuum that includes a trap for condensed water cooled at temperature of 5-7° C., a heating-cooling mantle, thermometer, and dosing funnel for liquids, in which is loaded at ambient temperature a predetermined quantity of technical grade maleic anhydride. The maleic anhydride is mixed at temperatures of about 75° C. for about 30 minutes to yield a transparent fluid mass of melted maleic anhydride. A persistent semi-opaque melt indicates the presence of maleic acid. Transforming maleic acid to maleic anhydride can be achieved by connecting the kneader to a vacuum distillation apparatus and adjusting the pressure to 400 mbar at the above temperature for about 30 minutes. The maleic anhydride melt at atmospheric pressure is brought to a temperature not less than 55° C. and not greater than 100° C. In another embodiment, the temperature is between 65° C. and 90° C. Technical grade styrene and dissolved initiator are added to the maleic anhydride melt over a period of time not less than 10 minutes and not greater than 60 minutes. In another embodiment, period of time is between 20 and 40 minutes. Mixing is continued at atmospheric pressure and a temperature not less than 60° C. and not greater than 150° C. for a period of time not less than 45 minutes and not greater than 300 minutes. In another embodiment the mixing temperature is maintained between 85° C. and 115° C. In another embodiment, the mixing time is between 60 and 180 minutes.

The yellow-brown, viscous and transparent reaction mass is processed to transform unreacted excess maleic anhydride to maleic acid by hydrolysis. The content of the kneader is cooled to not less than 55° C. and not greater than 85° C. by adding deionized water (with a conductivity less than 10 µS). In another embodiment, the content of the kneader is cooled to temperatures between 60° C. and 80° C. The amount of deionized water added is not less than 5% and not greater than 40% by weight versus the reaction mass. In another embodiment, the amount of deionized water added is between 10% and 35% by weight during a period of time not less than 30 minutes and not greater than 180 minutes. In another embodiment, the deionized water is added between 60 minutes and 120 minutes. After finishing dosing with the deionized water, the reaction mass is mixed for a period of time not less than 20 minutes and not greater than 90 minutes. In another embodiment, the reaction mass is mixed for a period of time between 30 minutes and 60 minutes. Alternatively, the reaction mass is cooled to ambient temperatures by circulating through the mantle liquid with temperatures of 5-7° C.

The maleic acid is then extracted from the content of the kneader according to the following process. A stainless steel mixing vessel equipped with a Nuce filter and having a useful volume three times larger than that of the kneader is used. The mixing vessel is further equipped with an impeller stirrer with two blades, a mantle for heating or cooling, a thermometer, a dosing nipple for liquids, an inlet-pipe connection for compressed air, an outlet nipple, and, in the interior, a filter based on two pierced stainless steel plates with a polyamide cloth (100 micron mesh) between them. The vessel is filled with deionized water (with a conductivity less than 10 µS) in an amount that is approximately six times the volume of the reaction mass at a temperature not less than 5° C. and not greater than 40° C. In another embodiment, the temperature is between 15° C. and 35° C. While stirring the deionized water moderately (stirrer speed=40-60 rpm) the reaction mass is added via the helical conveyer. The coarse, aqueous suspension formed is mixed for not less than 1 hour and not greater than 6 hours. In another embodiment, the suspension is mixed between 2 and 4 hours. The stirring is then stopped and the aqueous phase is eliminated by filtration under pressure.

The process is repeated for as many times as it takes to obtained a maleic acid content in the supernatant of less than 0.001% by weight as determined by volumetric titration with a solution of NaOH 0.01 N.

The wet solid, substantially free of the maleic acid, and with a humidity content of 70%, is transferred to a circular dryer equipped with a heating and cooling mantle, thermometer, helicoidally stirrer, breaking device with rotary knife, and is connected to a vacuum distillation apparatus comprising a filter with sackcloth, condenser, and collecting vessel for the condensation water. The granular mass is dried at a temperature of not less than 50° C. and not greater than 90° C. In another embodiment, the drying temperature is between 60° C. and 80° C., and the vacuum is at 50 mbar for a period of time not less than 4 hours and not more than 10 hours. In another embodiment, the drying period of time is between 6 and 8 hours. Lastly, the material is cooled to ambient temperature, removed from dryer, and packed in welded polyethylene bags.

The aqueous solution of maleic acid resulting from the extraction is processed by thermal dehydration to obtain maleic anhydride using one of the proceeding known methods in art and adapted to the present invention (see for example U.S. Pat. No. 3,993,671; U.S. Pat. No. 4,118,403; U.S. Pat. No. 4,414,898 or U.S. Pat. No. 4,659,433).

SMA Copolymers

SMA copolymers prepared in conformity with the methods described above have the following characteristics:
1. Sty:Mal=42:58-52:48 weight percent (styrene/[maleic anhydride+maleic acid]).
2. MAnh/Mal=0.17-0.79.
3. Viscosimetric molecular weight ($M_v$)=200,000-2,500,000.
4. Styrene residual=0.015-0.042 weight percent.
5. Mal (maleic anhydride+maleic acid) residual=0.045-0.2 weight percent.

The above characteristics were determined by the following procedures:
a) The amount of residual styrene was measured by extraction with benzene (spectroscopic grade) of 1 g of polymer for 12 hours by Sohxlet extraction. The benzene extractions were then analyzed by gas spectroscopy (Perkin-Elmer equipment).
b) The amount of residual maleic acid was measured by dialysis with distilled water of a 2 g sample of polymer at 40° C. using a Spectr/Por CE dialyze membrane in 14 cycles of 24 hours each (500 ml water per cycle), the water was changed after each cycle. The accumulated water was analyzed for maleic acid by HPLC method (WATERS equipment).
c) Monomeric concentration expressed as Sty:Mal (styrene: maleic comonomer [maleic anhydride+maleic acid]) was estimated by conductometric titration of a solution prepared by dissolving 0.1 g of dry polymer in a solution of NaOH 0.5 N and HCl 0.5N.
d) Functionality ratio, expressed as MAnh:Mal (maleic anhydride [maleic anhydride+maleic acid]), [(mol/g): (mol/g)], was estimated using FTIR quantitative analysis (SHIMAZU equipment): Maleic Anhydride p.a. (ACROSS) and Maleic Acid p.a.(ACROSS) versus the characteristic absorption bands: 1770-1790 $cm^1$ for anhydride and 1700-1720 $cm^1$ for COOH.
e) Viscosimetric average molecular weight, $M_v$, was estimated using the evaluation of intrinsic viscosity [$\eta_{rel}$] based on relative viscosity [$\eta$] of one solution of polymer with concentration c=0.5 g/100 ml in tetrahydrofuran at 25° C., using the calculus formulae (Raju K. V. S. N., Yaseen M. *J. Appl. Polym. Sci.*, 45, 677-681, 1992; Chee K. K. *J. Appl Polym. Sci.*, 34, 891-899, 1987 and Spiridon D. et al. *Polymer International*, 43, 175-181, 1997).

$$[\eta] = \frac{\sqrt{2(\eta_{rel} - \text{Ln}(\eta_{rel}) - 1)}}{c}$$

$$[\eta] = 0.77 * 10^{-4} * M_V^{0.725}$$

Further examples for realizing the invention are presented below.

EXEMPLIFICATION

Example 1

In a kneader-extruder apparatus (60 liters) connected to a vacuum that includes: a trap for condensed water cooled at temperatures of 5-7° C., a heating-cooling mantle, thermometer, and dosing funnel for liquids, 25 kg of technical grade maleic anhydride was added at ambient temperatures. The maleic anhydride was mixed and heated at 75° C. for about 30 minutes to obtain a transparent fluid mass of melted maleic anhydride. Technical grade styrene with 8 g of dissolved dibenzoyl peroxide was added under ambient pressure over 20 minutes bringing the temperature of the mixture to 65° C. After adding the styrene, the temperature of the reaction increased rapidly during a period of 15 minute from 78° C. to 116° C. due to polymerization. When the exothermic phase of polymerization is completed, mixing continued at atmospheric pressure at 100° C. for another 60 minutes. The reaction mass was a viscous, transparent, yellow brown solution which was cooled to 65° C. by adding 8 liters of deionized water (with a conductivity less than 10 μS) while mixing over 60 minutes. After finishing water dosing, the reaction mass was mixed for another 45 minutes at 65° C. Alternatively, the reaction mass can be cooled to ambient temperatures by circulating cooled water (5-7° C.) through the mantle of the kneader.

The reaction mass is transferred through the helical conveyer located in the interior central zone of the apparatus to a stainless steel vessel (Nutsche Filter) containing 160 liters of deionized water at 18° C. under moderate stirring (stirrer speed adjusted to 40-60 ppm). The Nutsche Filter has a useful volume three times larger than that of the kneader. The Nutsche Filter has a mantle for heating and cooling, a stirrer, a thermometer, a dosing nipple for liquids, an inlet-pipe connection for compressed air, an outlet nipple, and, in the interior, a filter media based on two pierced plates of stainless steel with a polyamide cloth between them (100 microns mesh). The coarse aqueous suspension was mixed for 2 hours. The aqueous phase was then removed by filtration under pressure.

The process was repeated 3 times. The last supernatant had a maleic acid concentration of only 0.00073% by weight.

The wet solid had a humidity content of 68.3% and was transferred to a circular dryer equipped with a heating and cooling mantle, thermometer, helicoidally stirrer, breaking device with a rotary knife and was connected to a vacuum. The wet mass was dried at 65° C. at 50 mbar for 5 hours. Lastly, the material was cooled to ambient temperature, removed from the dryer, and packaged in welded polyethylene bags.

The aqueous solution of maleic acid resulting from the extraction was collected for maleic anhydride recovery.

From this process, 5.17 kg SMA copolymer was obtained as a white powder: 94.598% SMA copolymer; 5.31% water; 0.029% styrene and 0.063% (maleic anhydride+maleic acid), all as weight percent. The purified SMA copolymer had the following structural characteristics: $M_y$=1,251,000; Sty:Mal=46:54 and MAnh:Mal=0.49.

Example 2

Same equipment and procedure as described in Example 1 except 3.4 liters of styrene having 6.8 grams of dibenzoyl peroxide dissolved therein was added at 80° C. Maximum temperature during the exothermic phase was 121° C. The last supernatant from the extraction had a maleic acid content of 0.00095% by weight and drying was at 80° C. for 6 hours.

The process yielded 6.28 kg of SMA copolymer as a white powder: 95.267% SMA; 4.63% water; 0.031 styrene and 0.072% (maleic anhydride+maleic acid), all as weight percent. The purified SMA copolymer had the following structural characteristics: $M_v$=546,000; Sty:Mal=48:52 and MAnh:Mal=0.68.

Example 3

Same equipment and procedure as in Example 1 except that 2.5 liters of styrene having 8.5 grams of initiator dissolved therein was added over 40 minutes. Maximum temperature during the exothermic phase was 128° C. Polymerization was complete after 180 minutes with a final temperature of 85° C. Hydrolysis utilized 6 liters of water added over 120 minutes and the extractions were made at 35° C.

The process yielded 4.72 kg of SMA copolymer as a white powder: 93.08% SMA; 6.82% water; 0.018% styrene and 0.082% (maleic anhydride+maleic acid), all as weight percent. The purified SMA copolymer had the following structural characteristics: $M_v$=726,000; Sty: Mal=51:49 and MAnh:Mal=0.27.

Example 4

In the same type of kneader-extruder apparatus that used in Example 1, 25 kg of technical grade maleic anhydride was loaded at ambient temperatures. The maleic anhydride was heated and mixed at 75° C. for 30 minutes to yield a fluid transparent mass of melted maleic anhydride. 3 liters of technical grade styrene having 9.8 grams of dibenzoyl peroxide dissolved therein was added at atmospheric pressure over a period of 40 minutes. After adding the styrene, the temperature of reaction increased rapidly from 83° C. to 132° C. over 12 minutes. After the exothermic phase of reaction was completed, mixing at atmospheric pressure at 115° C. continued for 120 minutes. At this time 9.8 liters of deionized water (with conductivity less than 10 μS) was added over 120 minutes cooling the reaction mass to 60° C. The reaction mass was mixed at 60° C. for 60 minutes at 60° C. Alternatively, the reaction mass can be cooled to ambient temperatures by circulating cooled water (5-7° C.) through the mantle.

The granular mass from the kneader was transferred through the helical conveyer to a vessel containing 160 liters of water at 15° C. under moderate stirring. The coarse aqueous suspension was mixed for 4 hours before removing the aqueous phase by filtration under pressure. This process was repeated 3 times. The last supernatant removed had a maleic acid content of 0.00091% by weight.

The purified wet solid had a humidity content of 72.8% and was transferred to a circular dryer connected to a vacuum and dried at 80° C. at 50 mbar for 4 hours. Lastly, the material was cooled to ambient temperature, removed from dryer, and packed in welded polyethylene bags.

The aqueous solutions of maleic acid from the extractions were collected for maleic anhydride recovery.

The process yielded 6.93 kg of SMA copolymer as a white powder: 92.114% SMA; 7.82% water; 0.021% styrene and 0.045% (maleic anhydride+maleic acid), all as weight percents. The purified SMA copolymer had the following structural characteristics: $M_v$=251,000; Sty:Mal=42:58 and MAnh:Mal=0.17.

Example 5

The same type of equipment and procedure as in Example 4 was used except 2.4 liters of styrene having 6.8 grams of dibenzoyl peroxide dissolved therein was added, the reaction mass was added to 2.1 liters of deionized water, and drying was carried out at 80° C. for 8 hours.

The process yielded 4.72 kg of SMA copolymer as a white powder: 96.121% SMA; 3.78% water; 0.041% styrene and 0.058% (maleic anhydride+maleic acid), all as weight percents. The purified SMA copolymer had the following structural characteristics: $M_v$=1,780,000; Sty:Mal=49:51 and MAnh:Mal=0.79.

We claim:

1. A styrene-maleic anhydride-maleic acid copolymer having less than 0.050% by weight unreacted styrene monomer and less than 0.090% by weight unreacted maleic anhydride and maleic acid combined.

2. The styrene-maleic anhydride copolymer of claim 1, wherein the weight percent of styrene monomer to maleic anhydride and maleic acid monomer as defined as styrene/(maleic anhydride+maleic acid) is 42:58-52:48.

3. The styrene-maleic anhydride copolymer of claim 1, wherein the viscosimetric molecular weight, $M_v$, of the copolymer is 200,000-1,800,000.

4. An article of manufacture comprising the styrene-maleic anhydride copolymer of claim 1.

5. The article of manufacture of claim 4, used in the field of medical bioengineering, tissue engineering, pharmaceutical products, body hygiene, cosmetics, biotechnology, food industry, agriculture, or absorbent textiles.

6. A method of preparing a styrene-maleic anhydride-maleic acid copolymer having less than 0.050% by weight unreacted styrene monomer and less than 0.090% by weight unreacted maleic anhydride and maleic acid combined, said method comprising the steps of:
   a) melting an amount of maleic anhydride monomer;
   b) adding an amount of styrene containing dissolved initiator to the maleic anhydride; and
   c) stirring the maleic anhydride, styrene, and initiator mixture for an effective amount of time to form the styrene-maleic anhydride-maleic acid copolymer.

7. The method of claim 6, wherein the initiator is a free radical initiator.

8. The method of claim 6, wherein the initiator is selected from the group consisting of diacyl peroxides, dibenzoyl peroxide, di-tertbutyl peroxide, tert-butyl perbenzoate, tert-butyl perethylhexanoate, peresters, tert.-butyl perpivalate, aliphatic azo, azoisobutyronitrile, azo-4-cyanopentanoic acid, peroxodisulphuric acid, and hydrogen peroxide.

9. The method of claim 6, wherein the amount of styrene:maleic anhydride is between 1:6 and 1:14 by weight.

10. The method of claim 6, wherein the amount of initiator is between 0.01% and 0.05% versus the weight of the reaction mass.

11. The method of claim 6, wherein melting the maleic anhydride is carried out by heating the maleic anhydride at least 75° C.

12. The method of claim 6, wherein the styrene is added to the maleic anhydride between 55° C. and 100° C.

13. The method of claim 6, wherein the styrene is added to the maleic anhydride over a period of time between 10 minutes and 60 minutes.

14. The method of claim 6, wherein the mixing of the maleic anhydride, styrene, and initiator is carried out at atmospheric pressure and at a temperature between 60° C. and 150° C. for a period of time between 45 minutes and 300 minutes.

15. The method of claim 6, further comprising the step of allowing the styrene-maleic anhydride copolymer formed in step c) to cool to a temperature between 55° C. and 85° C.

16. The method of claim 6 further comprising hydrolyzing at least a portion of the maleic anhydride to maleic acid by adding water to the styrene-maleic anhydride copolymer.

17. The method of claim 16, wherein the amount of water is between 5% and 40% by weight of the styrene-maleic anhydride copolymer.

18. The method of claim 16, wherein the water is added over a period of time between 30 and 180 minutes.

19. The method of claim 16, wherein after the water is added to the copolymer the mixture is mixed for a period of time between 20 and 90 minutes.

20. The method of claim 16, further comprising purifying the copolymer by extracting free maleic acid with water.

21. The method of claim 20, wherein the copolymer is mixed with a quantity of water about 6 times the weight of the copolymer at a temperature between 5° C. and 40° C. before removing the water.

22. The method of claim 21, wherein the water is removed by filtration under pressure.

23. The method of claim 20, wherein the extraction is repeated until the content of maleic acid in the supernatant is less than 0.001% by weight.

24. The method of claim 20, further comprising a drying step wherein the copolymer is dried at a temperature between 50° C. and 90° C.

* * * * *